United States Patent [19]

Mateik et al.

[11] Patent Number: 4,756,305
[45] Date of Patent: Jul. 12, 1988

[54] EYE TRAINING DEVICE

[76] Inventors: William J. Mateik, 353 Benjamin Rd.; Scott A. Greenwood, 350 Benjamin Rd., both of Winchendon, Mass. 01475

[21] Appl. No.: 910,622

[22] Filed: Sep. 23, 1986

[51] Int. Cl.⁴ .............................................. A61B 3/08
[52] U.S. Cl. ................................... 128/25 A; 128/76.5
[58] Field of Search .................... 128/1 R, 25 A, 76.5; 350/133, 331; 351/203

[56] References Cited

U.S. PATENT DOCUMENTS

| | | | |
|---|---|---|---|
| 2,831,481 | 4/1958 | Radin | 351/203 |
| 2,897,816 | 8/1959 | Williams | 128/76.5 |
| 4,148,565 | 4/1979 | Gunst | 128/25 A X |
| 4,294,522 | 10/1981 | Jacobs | 128/25 A X |
| 4,402,580 | 9/1983 | Ross | 351/203 |
| 4,506,963 | 3/1985 | Cooper | 128/76.5 |
| 4,561,723 | 12/1985 | Hamano et al. | 350/133 X |

FOREIGN PATENT DOCUMENTS

| | | | |
|---|---|---|---|
| 2159004 | 6/1973 | Fed. Rep. of Germany ... | 128/25 A |
| 1446131 | 8/1976 | United Kingdom ............ | 128/25 A |
| 1454273 | 11/1976 | United Kingdom ............ | 128/76.5 |

Primary Examiner—Edward M. Coven
Attorney, Agent, or Firm—Joseph S. Iandiorio; Douglas E. Denninger

[57] ABSTRACT

An eye training device for treating one or more visual disorders in a patient, which displays two images visually superimposable into a single image and optically conducts one of the images to a right eye viewing port and the other image to a left eye viewing port. The device further includes an assembly for modifying the perception of one or both images by the patient to differ from the perception required for normal viewing of the images to exercise corresponding one or both eyes of the patient. At least one of the first and second images has a first image element whose location is changeble relative to the other image elements, and the device further includes a mechanism which is operable by the patient to move the first image element while the patient views through the viewing ports.

47 Claims, 5 Drawing Sheets

EYE TRAINING DEVICE

FIELD OF INVENTION

This invention relates to a device for treating visual disorders, and more particularly to such a device which requires the active participation of the patient using the device.

BACKGROUND OF INVENTION

Many people with visual disorders never have those disorders improved. Corrective lenses establish normal visual acuity for many people, but the underlying visual disorder persists. Lenses alone cannot compensate for some disorders.

Presently, treatment of such disorders as strabismus, amblyopia, myopia, and accommodative insufficiency is accomplished through widely varying techniques. Strabismus, known as cross-eyes, is the condition where the visual axes of the eyes cannot be directed to the same object at the same time and is due to a lack of muscular coordination. One eye turns either vertically or horizontally relative to the other eye. Strabismus is typically caused by genetics, injury or disease which results in a misalignment of one or more of the six pairs of ocular muscles controlling the eyeball. Double vision or suppression of the strabismic eye often results.

Strabismus can be treated through surgery. Surgery is expensive, invasive, and has a surprisingly low rate of effectiveness. Over 85% of the operations do not provide effective treatment for strabismus. Most surgery simply treats strabismus cosmetically by physically reorienting the eyeball, but the patient is still not using both eyes together as a unit. Any underlying amblyopia which frequently accompanies strabismus remains untreated.

Amblyopia involves reduced vision in one eye, typically because of mental suppression. The brain partially or completely ignores optic nerve signals from that eye. Amblyopia is frequently induced by strabismus or by a high refractive error in only one eye.

Amblyopia results in poor visual efficiency due to decreased stereopsis and poor distance judgment. This condition is frequently treated by patching the good eye to force the brain to utilize the amblyopic eye. Recent studies indicate, however, that such treatment can induce amblyopia in the patched eye.

Myopia, known as nearsightedness, is a refractive disorder where the eye focuses incoming light to a point in front of the retina. Blurred distance vision results because the refractive system of the myopic eye remains excessively convex, that is, it converges light too quickly, when distant objects are viewed. Some progress has been made with biofeedback techniques which attempt to train the muscles controlling the shape of the lens of the eye. A biofeedback instrument, however, typically costs upward of $15,000. Myopia is correctable with lenses but is not improved. The American Optometric Association estimates that two to four percent of children under six years of age have amblyopia and that 40% of the total population of the United States are likely to develop myopia.

Accommodation is an involuntary adjustment of the eye to focus the image of an object on the retina. In accommodation for near vision, the ciliary muscle contracts to reduce tension on the lens and allow it to become steeper, that is, to become more convex. Several factors reduce the accommodative mechanism. During the normal aging process the lens becomes stiffer. Environmental, genetic and other factors can increase lens stiffness or weaken the ciliary muscle. These result in headaches and discomfort when working on near tasks such as reading or focusing on a computer screen.

The field of vision training involves therapy to improve conditions such as strabismus and amblyopia. The optometrist prescribes visual tasks to be practiced under controlled conditions. In-office training is recommended for most patients and especially those with strabismus and amblyopia. Home training is particularly not effective for children since they lose interest in the training and have difficulty monitoring their progress.

There are several large instruments for analyzing strabismus, amblyopia, myopia and accommodation disorders. Two of such devices are the VS-II Vision Screener and the Opthalmic Telebinocular, available from Keystone View, Davenport, Iowa. The Vision Screener occupies over one-half cubic foot of space, weighs more than ten pounds, and must be plugged into a wall outlet. It has a viewing head with a forehead rest and a lens system with one viewing distance of 15 inches and another of 6 meters, equivalent to optical infinity. Static targets on test slides are illuminated by reflected light. The vision screener tests for visual acuity, phorias, fusion, depth perception and color perception. Images for the left and right eye are successively presented on a rotating target drum.

The Opthalmic Telebinocular is much larger and again uses static targets. An occluder is provided for each eye to permit monocular testing or vision training. A patient is quickly bored when vision training is conducted on this and similar instruments. Since improvements in vision depend heavily on the motivation of the patient and the frequency of therapy, progress is typically quite slow. Further, the training sessions must be conducted in the office of the optometrist or ophthalmologist.

SUMMARY OF INVENTION

It is therefore an object of this invention to provide an improved eye-training device for treating a number of visual disorders.

It is a further object of this invention to provide such a device which provides effective treatment for amblyopia without inducing amblyopia in the good eye of a patient.

It is a further object of this invention to provide such a device which non-invasively treats strabismus.

It is a further object of this invention to provide such a device which can improve accommodation in a patient.

It is a further object of this invention to provide such a device which can reduce myopia.

It is a further object of this invention to provide such a device which can be used at home or other location outside a doctor's office during vision training.

A still further object of this invention is to provide such a device which is relatively inexpensive and can be hand-held.

It is a further object of this invention to provide such a device which is more stimulating to use than conventional devices.

Yet another object of this invention is to provide such a device which interacts with the patient.

It is a further object of this invention to provide such a device which can monitor the progress of a patient through scoring which in turn depends on the visual acuity and quality of visual exercise of the patient.

This invention results from the realization that truly effective, non-invasive treatment of several visual disorders can be achieved by a device which displays an image for each eye of a patient, alters the perception of one or both images beyond that required for normal viewing of the images to strengthen the vision of the patient, and requires the patient to control the location of an image element to encourage the patient to concentrate visually on the image element.

This invention features an eye training device for treating one or more visual disorders in a patient. There is image display means for displaying first and second images visually superimposable into a single image, at least one of the first and second images having a first image element whose location is changeable relative to the other image elements. The device further includes image viewing means for optically conducting one of the images to a right eye viewing port and conducting the other image to a left eye viewing port. There is also means, associated with the viewing means, for modifying the perception of one or both images by the patient to differ from the perception required for normal viewing of the images to exercise corresponding one or both eyes of the patient. The device further includes operator means for controlling the location of the first image element, the operator means operable by the patient to move the first image element while the patient views through the viewing ports.

This invention also features an eye training device for treating strabismus in a patient, including image display means, image viewing means, and refractor means, associated with the viewing means, for laterally displacing by a selected diopteric amount one of the images relative to the strabismic eye of the patient. The device further includes operator means for controlling the location of the first image element while the patient observes the first and second images through the viewing ports.

In one embodiment, the first and second images include differing and parallactically displaced portions of a common image, and only one of the images has the first image element. Alternatively, the first and second images are parallatically displaced views of the same images and both the images have the first image element. The image display means may include means for altering the location of other image elements in at least one of the first and second images such as image signal means for generating location control signals and means, responsive to the location control signals, for varying the location of the other image elements. The means for altering may be responsive to the location of the first image element relative to the other image elements and further includes means for producing a penalty when the first image element shares a location with one of the other image elements. The means for producing may include means for disrupting the first image element when it shares a location with one of the other image elements. The patient must repeatedly move the first image element to preserve it from disruption.

In another embodiment, the refractor means includes a variable prism assembly and locking means for securing the refractor means in position. The right and left eye viewing ports are spaced apart with respect to each other to enable binocular use of the device by the patient.

In yet another embodiment, the training device is also useful for treating amblyopia and further includes means, associated with the viewing means, for occluding image conduction to the viewing port of a non-amblyopic eye of the patient. The means for occluding may include a removable optically opaque element, or filter means for controllably diminishing the conduction of one of the images to the corresponding viewing port for the non-amblyopic eye. The first and second images may be transmitted as polarized light and the filter means includes polarizing means positionable to have an axis of polarization different from that of the polarized light. The axis of polarization of the polarizing means may be adjustable. The image display means may include a liquid crystal display.

In another embodiment, the image viewing means includes refractor lens means proximate each viewing port for establishing normal refractory viewing of the first and second images at a selected viewing distance. The device may further include a refractory corrective lens, located proximate at least one of the viewing ports, for compensating for refractive errors of one or both eyes of the patient. The refractor lens means may establish a viewing distance as a reading distance or as optical infinity. The device may be usable for treating myopia and may include concave lens means, located proximate at least one of the viewing ports, for partially compensating for myopic refractive errors of one or both eyes of the patient. The device may further include a housing for carrying the image display means, the image viewing means and the refractor means, the housing being of a shape and size holdable by the hands of the patient during use of the device.

This invention further features a device for enhancing accommodation in a patient, including image display means for displaying first and second images visually superimposable into a single image, image viewing means, and a bifocal lens assembly for relaxing the accommodative mechanism in one or both eyes of the patient. In a first position relative to the left and right eye viewing ports and for stimulating the accommodative mechanism in a second position. The device further includes means for moving the bifocal lens assembly to and from the first and second positions.

In one embodiment, at least one of the first and second images has a first image element whose location is changeable relative to the other image elements, and the device further includes operator means for controlling the location of the first image element. Bifocal lens assembly may include a convex lens for relaxing the accommodative mechanism and a concave lens for stimulating the accommodative mechanism. In another embodiment, the means for moving includes user activation means actuatable by the patient to move the bifocal lens assembly. Activation means may include linkage means connected proximate in the first end to the bifocal lens assembly, and user control means, connected proximate a second end for the linkage means, for selectively relocating the second end. The device may further include means for rewarding the patient when the user activation means is actuated at a preselected rate. The bifocal lens assembly may provide the same relaxation and stimulation for both eyes and the image viewing means may include refractor lens means proximate each eye viewing port for establishing normal refractory viewing for the first and second images at a selected viewing distance such as a reading distance.

DISCLOSURE OF PREFERRED EMBODIMENTS

Other objects, features and advantages will occur from the following description of preferred embodiments and the accompanying drawings, in which.

This invention may be accomplished by a device which displays two images visually superimposable into a single image, where one or both of the images exhibits a vehicle or other object whose movement is controlled by the patient when operating the device. The device includes optical conduits for optically conducting one image to the right eye viewing port and the other image to a left eye viewing port. Within the optical conduit are lenses, prisms, filters, or other elements for modifying the perception of one or both images by the patient to differ from the perception required for normal viewing of the images, depending on the visual disorder to be treated. The preception can be modified, in other words, by various types of refractive distortion or occlusion.

An eye training device according to this invention encourages and even tempts the patient to perform eye exercises. In one construction the patient actually plays a game while performing the eye exercise. A device from the field of electronic games, such as the stereoscopic viewing device of Hamano et al., U.S. Pat. No. 4,561,723, can be modified according to this invention. The device of Hamano et al. displays parallactically displaced views of an image selectively transmitted by a liquid crystal display. Lenses in the left and right viewing ports establish normal perception for both eyes of a person playing a game on the device. The device provides two slightly different views of the same image to provide a stereoscopic effect. Individual elements in both views change in concert to provide the appearance of motion for those elements. No suggestion is made in that patent or other prior art for modifying the game for use as a vision trainer.

Figure 1A:
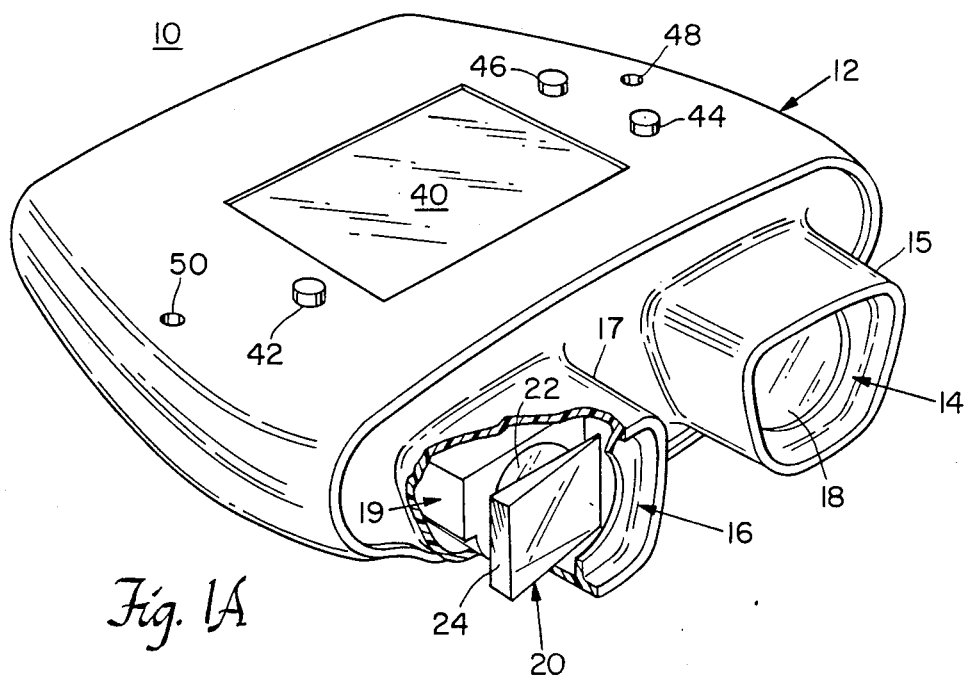
FIG. 1A is a partial-cutaway, axonometric view of an eye training device according to this invention for treating strabismus using removable prisms.

Eye training device 10 according to this invention, FIG. 1A, is constructed to treat strabismus and includes hand-held housing 12 and viewing ports 14, 16 within lens assembly housings 15, 17. Protective outer glass lens 18 is shown in viewing port 14 but is removed from viewing port 16 to reveal prism 20 and refractive lens 22. Refractive lens 22 is part of lens assembly 19 which establishes normal refractory viewing of images produced within housing 12. The viewing distance established by lens 22 can range from reading distance, e.g., 16–18 inches, to optical infinity, i.e. twenty feet or more.

Figure 1B:
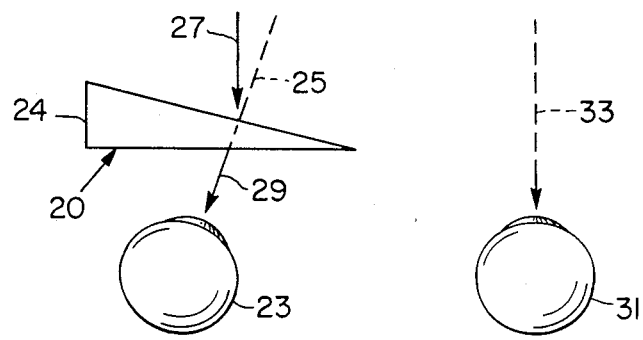
FIG. 1B is a schematic top plan view of the prism shown in FIG. 1A laterally displacing an image for an inwardly turned eye.

Normal refractory viewing of images within housing 12 is altered by the addition of a refractive element such as block prism 20. Base 24 of prism 20 is shown oriented toward the left side of device 10. Such a "base off" or "base out" orientation bends light transmitting images within housing 10 to the right, which laterally displaces the image toward the base as shown in FIG. 1B. Left eye 23 is turned in as indicated by visual axis 25. Prism 20 displaces incoming light ray 27 to parallel the visual axis 25 as shown for ray 29. Right eye 31 has a normal visual axis 33. Such an arrangement is suited for a patient having a strabismic eye whose visual axis turns in. Prism 20 can be oriented "base down" or "base up" to compensate for a vertically oriented strabismic eye or "base in" for eyes whose visual axis turns out.

During treatment of the patient with strabismus, it is preferable to first treat any underlying amblyopia, as described below. Once the brain is properly using the strabismic eye, prism 20 is initially selected to provide slightly less than full correction, enabling the patient to normally perceive images within housing 12 using a slight amount of effort. Strabismic eye deviations are typically measured in terms of diopters. A 1.0 diopter lens will focus parallel light rays one centimeter apart to a point at a distance of one meter. A greater diopteric amount indicates that the prism has a shorter focal length.

Figure 1C:
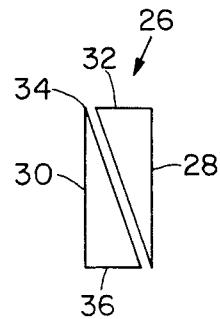
FIG. 1C is a schematic side view of a variable prism for use in the device of FIG. 1A.

Each week the patient should be checked for improvement and the diopteric amount reduced accordingly such as by substituting a different prism for prism 20 or altering a variable prism such as shown schematically in FIG. 1C. A variable prism 26, such as a Risley prism, has two prism segments 28, 30 movable relative to each other. When base 32 of prism segment 28 is aligned with apex 34 of prism segment 30, variable prism 26 produces a 0.0 diopter deviation of light. When base 36 is aligned with base 32, however, a maximum deviation is produced.

The strength of the prisms should be gradually reduced over time until 0.0 diopters are achieved. In some situations it is desirable to continue the progression to the opposite base direction to further strengthen the strabismic eye. As described below, it is preferable to have some mechanism for locking the prism in place so that the prism can be adjusted only by the optometrist or other attending doctor. A strabismic eye exhibiting a deviation of 10.0 diopters base out can be treated with a first prism providing 8.0 diopter base out correction. This prism is eventually replaced with a 6.0 D base out prism, a 4.0 D base out prism, eventually a 2.0 D base in prism.

Figure 3:
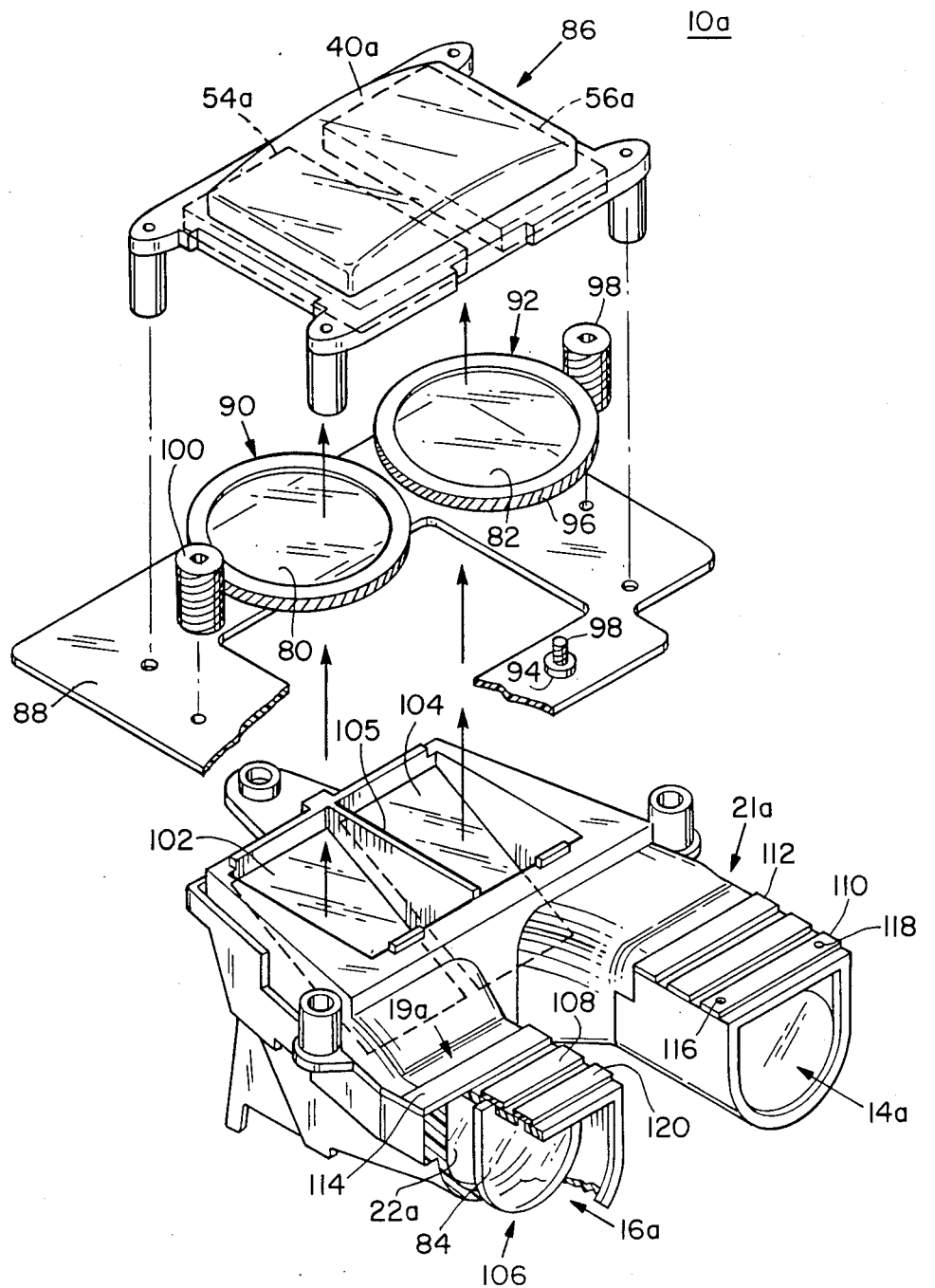
FIG. 3 is a partial exploded view of another eye training device according to this invention for treating amblyopia and myopia.

Except for the optical elements provided according to this invention, device 10 is similar to the electronic stereoscopic viewing device disclosed in U.S. Pat. No. 4,561,723 by Hamano et al., which is incorporated herein by reference. Translucent screen 40 admits ambient light which passes through an image slide whose image elements are selectively transmitted by a liquid crystal display. Control buttons 42, 44 and 46 allow the patient to interact with the images. Access ports 48, 50 are described below in relation to FIG. 3. An eye training device according to this invention is not limited to an image display screen having a liquid crystal display, however.

Figure 2:
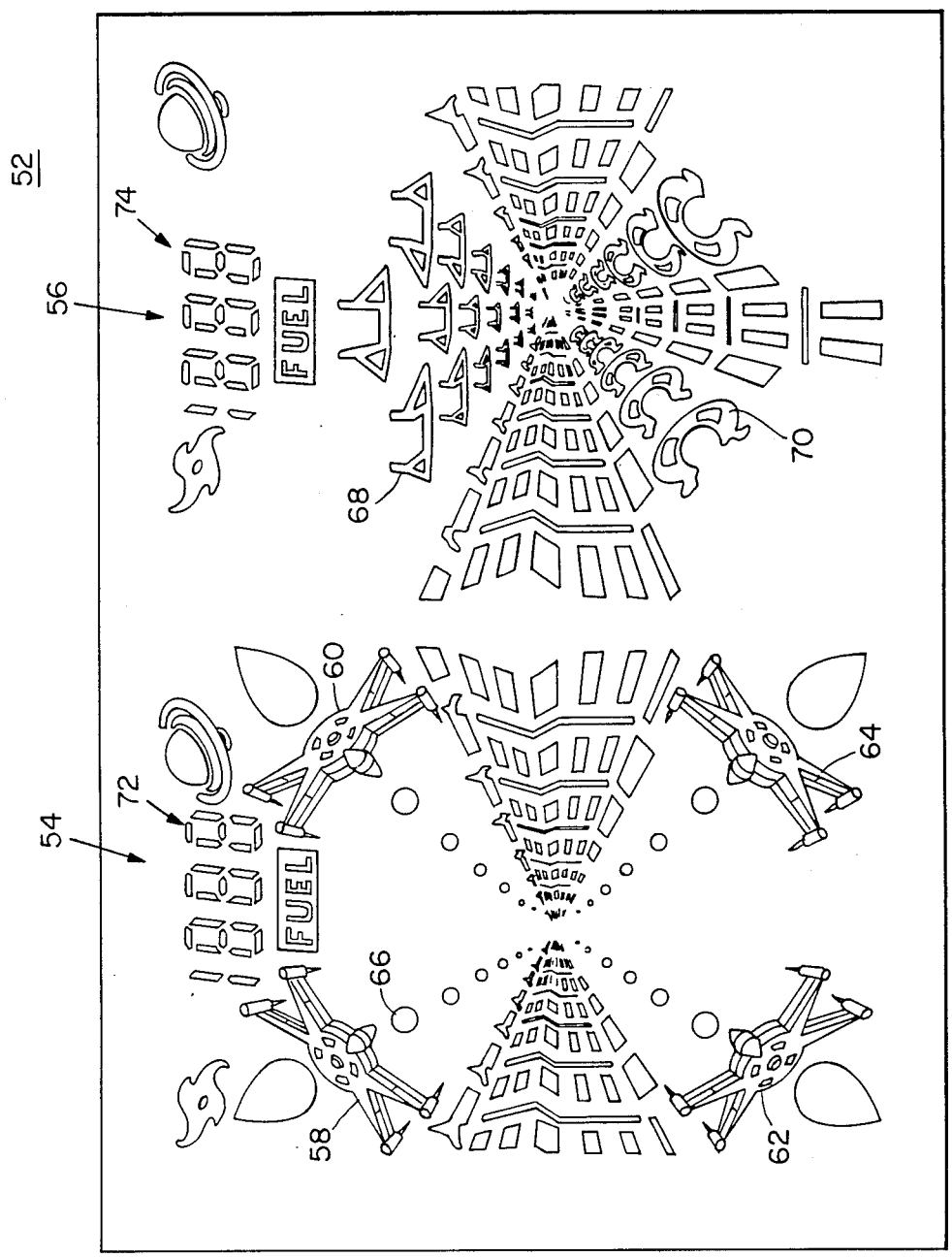
FIG. 2 is a diagram of left and right images which differ from each other yet which are integratable.

The two images produced by device 10 can be parallactically displaced views of the same image, or differing and parallactically displaced portions of a common image such as shown in FIG. 2. Image slide 52 contains left eye image 54 and right eye image 56. Left image 54 includes space ships 58, 60, 62 and 64, which can be alternatively activated by the patient to fire projectiles such as projectile 66. Right screen 56 contains enemy space ships such as space ships 68 and 70. During use of the eye training device, the patient must visually integrate, that is, superimpose, images 54, 56 in order to successfully operate the eye training device. The inability to properly combine images 54, 56 results in improper maneuvering of space ships 58, 60, 62 and 64, which in turn results in a lower score or destruction of the patient's space ship. The progress of the patient is evidenced by score elements 72, 74.

As described above, amblyopia typically accompanies strabismus. Eye training device 10a, FIG. 3, can be used to treat amblyopia and includes polarized filters 80, 82 and occluder member 84 for partially or totally occluding perception of one of the images by the non-amblyopic eye of the patient.

Image display assembly 86 mounts on support member 88 which in addition rotatably supports polarized filter assemblies 90, 92 containing filters 80, 82, respectively. Rotatable mounting pin 94, for example, supports frame 96 of filter assembly 92. Post 98 of rotatable support pin 94, rim 96, and drive gear 98 possess matching teeth which intermesh with each other. Drive gears 98, 100 are accessed through ports such as access ports 48, 50 shown in FIG. 1A. Such an arrangement allows the attending optometrist to carefully adjust the filters, such as with an Allen wrench, while reducing the likelihood that the patient will improperly readjust the filters. Alternatively, a portion of rim 96, for example, protrudes through housing 12 to allow manual rotation of filter assembly 92.

Image display assembly 86 contains a liquid crystal display between two polaroid sheets having their axes of polarization oriented normal to each other. The liquid crystal display is selectively excited by digital logic such as described in U.S. Pat. No. 4,561,723 to selectively transmit portions of the left and right images as polarized light. When the axes of polarization of filters 80, 82 are parallel with the axis of polarization of the lower polaroid sheet within display assembly 86, the images are fully transmitted through filters 80, 82 and reflected by mirrors 102, 104 so that the images may be perceived through viewing ports 14a, 16a. Optical partition 105 prevents interconduit optical contamination.

During treatment of amblyopia, the better, non-amblyopic eye is initally completely blocked. For a patient with an amblyopic right eye, the better left eye can be blocked by rotating filter assembly 90 by 90° or by inserting opaque occluder member 84 into receptacle 106. Occluder member 84 is secured in place by access cover 108. Later, opaque member 84 is replaced with an optically translucent member to reduce but not totally occlude viewing through port 16a, or filter assembly 90 is rotated to control the amount of light permitted to enter the left eye. While still theoretical, decreasing the amount of light transmitted to the better eye should decrease the visual acuity which in turn should stimulate use of the amblyopic right eye.

Amblyopia can also be induced by a high refractive error in one eye. Lens assemblies 19a, 21a are shown with multiple access covers for inserting a corrective lens such as a standard trial lens of 40 mm diameter. Therefore, a corrective lens can be placed beneath access cover 112 to replace the standard refractory lens similar to lens 22a beneath cover 114. Alternately, the corrective lens is placed beneath cover 110. All access covers can be provided with a locking mechanism such as screws placed through holes 116, 118 for access cover 110.

Eye training device 10a can be constructed to treat other visual disorders in addition to amblyopia. As described above, strabismus can be treated by inserting block prisms into one or both of the receptacles of lens assemblies 19a, 21a. After amblyopia is cured through use of occluder element 84 and/or filter assemblies 90, 92, the prism can be gradually decreased in strength until 0.0 lateral displacement is achieved.

Myopia can be controlled, in theory, by inserting a concave trial lens into the receptacles beneath access covers 110, 120. Under the supervision of the attending optometrist, the concavity of the corrective lenses is gradually decreased to encourage the patient to relax the lens of the myopic eye to place the lens in a less convex shape. It is desirable to have the game sufficiently intricate so that the game cannot be played if images are blurred. In another construction, lens assemblies 19a, 21a are removable and interchangeable with other lens assemblies providing different refractory correction.

The viewing distance of images observed through viewing ports 14a, 16a, must be at optical infinity when correcting myopia. The viewing distance for amblyopia and strabismus is not important for treating those disorders. Preferably, a game played on device 10a requires high visual resolution by the patient to encourage the patient to alter the shape of the lens of the myopic eye.

Figure 4:
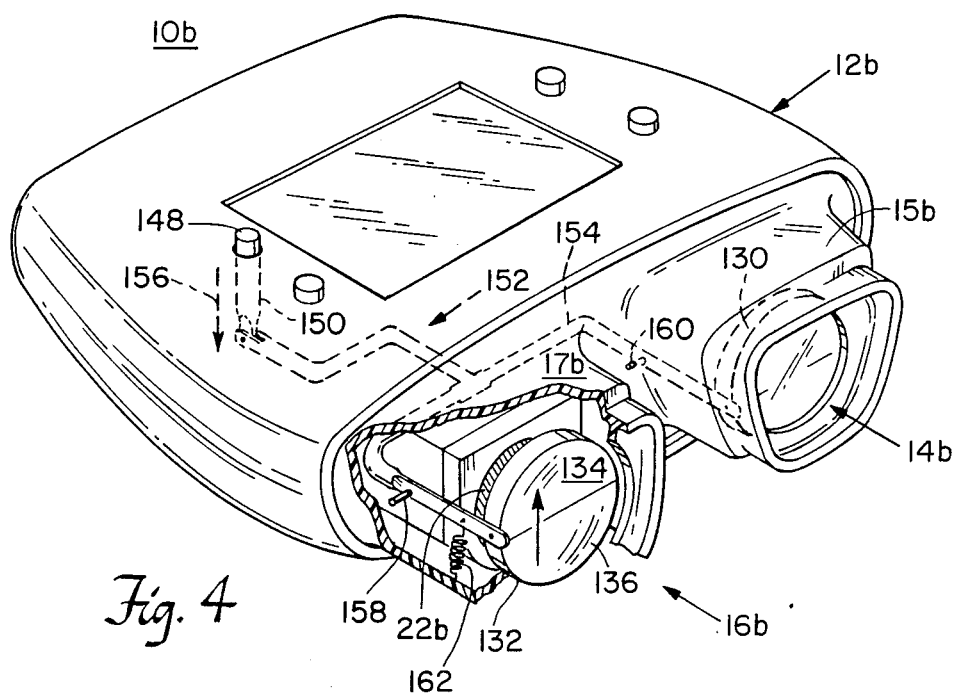
FIG. 4 is a partial cutaway, axonometric view of yet another eye training device according to this invention for use in enhancing accommodation.
Figure 5A:
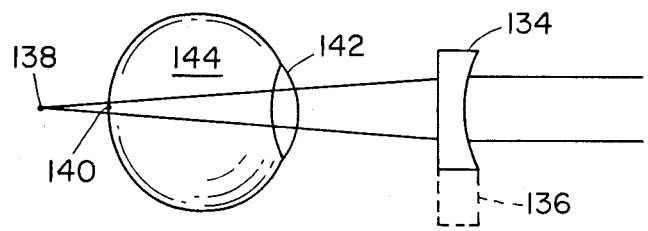
FIG. 5A is a schematic ray diagram of the increased focal length provided by one portion of the bifocal lens assembly shown in FIG. 4.
Figure 5B:
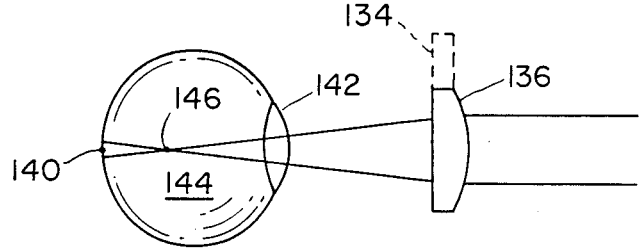
FIG. 5B is another ray diagram showing the decreased focal length provided by the other lens of the bifocal lens assembly.

Accommodation can be treated by using eye training device 10b, FIG. 4. Lens assembly housings 15b, 17b are enlarged to permit translation of bifocal lens assemblies 130, 132. Bifocal lens assembly 132 in this construction includes concave lens 134 and convex lens 136. The effect of these lenses is shown in FIGS. 5A and 5B. Concave lens 134 focusses light to point 138, which is located beyond retina point 140. Lens 142 of eyeball 144 is therefore stimulated to force lens 142 to become increasingly convex to focus the light to retina point 140. In contrast, concave lens 136 relaxes the accommodative mechanism and allows the lens to become less convex to shift focal point 146 to match retina point 140.

Lenses 134, 136 in this construction are integrally connected. Alternatively, the lenses are separated from each other such as in a flipper arrangement. Refraction of +1.00 D for lens 136 and −1.00 D for lens 134 is acceptable.

During use of eye training device 10b, the patient operates control button 148 which depresses push rod 150. Push rod 150 is part of the linkage system 152 which includes bracket 154 connected to bifocal lens assemblies 130, 132. As button 148 is depressed in the direction indicated by arrow 156, bracket 154 pivots about pivot points 158, 160 to move concave lens 134 above the optical pathway viewing axis passing through lens 22b and brings concave lens 136 into the viewing axis. When accommodation button 148 is released, spring 162 draws concave lens 134 back into the viewing axis.

Other constructions will be apparent to those skilled in the art, such as providing a dial wheel or a toggle switch in place of button 148, and using gears or an electric motor arrangement instead of linkage 152. Further, controls can be provided on either side of housing 12b to allow the patient to alternate the fingers used to translate bifocal lens assemblies 130, 132. In all constructions for enhancing accommodation, however, it is preferable for the viewing distance to be set at a reading distance of 16–18 inches to exercise the eye's ability to focus on near objects. It is desirable to have the game sufficiently intricate so that the game cannot be played if images are blurred. In addition, it is desirable to provide a higher score for a patient who alternates between lenses 134,136 at the proper rate. For instance, housing 12b can be provided with a counter associated with button 148 such as shown in FIG. 6.

Figure 6:
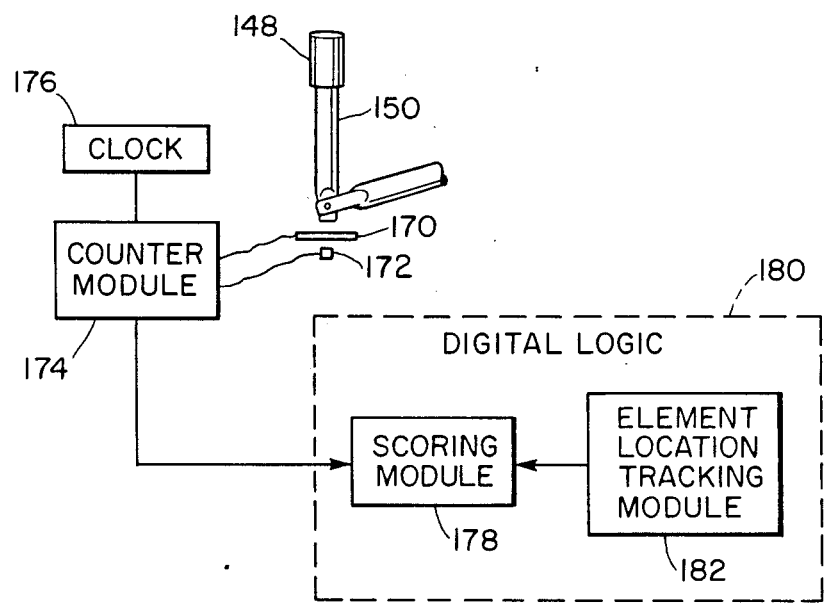
FIG. 6 is a schematic diagram of a scoring system which accounts for proper usage of the device of FIG. 4.

As shown in FIG. 6, push rod 150 closes contacts 170, 172 when button 148 is depressed. Counter module 174 compares the rate of contact closure with timing provided by clock 176 when button 148 is depressed at the proper rate, such as once every one or two seconds. Scoring module 178 of digital logic module score not only based on the conventional tracking of the image elements provided by tracking module 182, but increments or decrements the score also based on commands from counter module 174. The score of the patient is rewarded when button 148 is actuated at a preselected rate and penalized not only for improperly avoiding oncoming objects with the vehicle, but also for misusing control button 148.

Moreover, an eye training device according to this invention can be constructed to treat, in theory, phorias such as exophoria, in which the visual axes of the eyes tend to diverge outward. A phoria is different from strabismus in that the individual with a phoria is able to use both eyes but must work the occular muscles harder than normal to make the eyes function together as a unit. A person with strabismus is unable to overcome the disorder. Other minor disorders such as convergence insufficiencies can also be treated. Lenses for patients with these visual disorders can be selected, as is within the skill of the art, and combined with other components of an eye training device according to the invention.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. An eye training device for treating strabismus in a patient, comprising:
   image display means for displaying first and second images visually superimposable into a single image, at least one of said first and second images having a first image element whose location is changeable relative to other image elements;
   image viewing means for optically conducting one of said images to a right eye viewing port and conducting the other image to a left eye viewing port;
   refractor means, associated with said viewing means, for laterally displacing by a selected diopteric amount one of said images relative to the strabismic eye of the patient; and
   operator means for controlling the location of said first image element, said operator means operable by the patient to move said first image element while the patient observes said first and second images through said viewing ports.

2. The training device of claim 1 in which said first and second images include differing and parallactically displaced portions of a common image, and only one of said images has said first image element.

3. The training device of claim 1 in which said first and second images are parallactically displaced views of the same image and both said images have said first image element.

4. The training device of claim 1 in which said image display means includes means for altering the location of other image elements in at least one of said first and second images.

5. The training device of claim 4 in which said means for altering includes:
   image signal means for generating location control signals; and
   means, responsive to said location control signals, for varying the location of said other image elements.

6. The training device of claim 5 in which said means for altering is responsive to the location of said first image element relative to said other image elements, and further includes means for providing a positive response to the operator as long as said first image element is maintained in a location separate from one of said other image elements.

7. The training device of claim 6 further including means for producing a negative response to the operator when said first image element shares a location proximate one of said other image elements.

8. The training device of claim 7 in which said means for producing includes means for disrupting said first image element when it shares a location with one of said other image elements.

9. The eye training device of claim 8 in which said means for altering substantially continuously alters the location of said other image elements.

10. The training device of claim 1 in which said refractor means includes a variable prism assembly.

11. The training device of claim 1 further including locking means for securing said refractor means in position.

12. The training device of claim 1 in which said right and left eye viewing ports are spaced apart with respect to each other to enable binocular use of said device by the patient.

13. The training device of claim 1 which is also usable for treating amblyopia and further includes means, associated with said viewing means, for occluding image conduction to the viewing port of the non-amblyopic eye of the patient.

14. The training device of claim 13 in which said means for occluding includes a removable optically opaque element.

15. The training device of claim 13 in which said means for occluding includes filter means for controllably diminishing the conduction of one of said images to the corresponding viewing port for the non-amblyopic eye.

16. The training device of claim 15 in which said image display means includes means for transmitting said first and second images as polarized light and said filter means includes polarizing means positionable to have an axis of polarization different from that of said polarized light.

17. The training device of claim 16 in which said polarizing means has an adjustable axis of polarization.

18. The training device of claim 1 in which said image display means includes a liquid crystal display.

19. The training device of claim 1 in which said image viewing means includes refractor lens means proximate each viewing port for establishing normal refractory viewing of said first and second images at a selected viewing distance.

20. The training device of claim 19 further including a refractory corrective lens, located proximate at least one of said viewing ports, for compensating for refractive errors of one or both eyes of the patient.

21. The training device of claim 19 in which said refractor lens means establishes said viewing distance as a reading distance.

22. The training device of claim 19 in which said refractor lens means establishes said viewing distance as optical infinity.

23. The training device of claim 22 which is also usable for treating myopia and further includes concave lens means, located proximate at least one of said viewing ports, for partially compensating for myopic refractive errors of one or both eyes of the patient.

24. The training device of claim 1 further including a housing for carrying said image display means, said image viewing means and said refractor means, said housing being of a shape and size holdable by the hands of the patient during use of said device.

25. An eye training device for treating one or more visual disorders in a patient, comprising:
   image display means for displaying first and second images visually superimposable into a single image, at least one of said first and second images having a first image element whose location is changeable relative to other image elements;
   image viewing means for optically conducting one of said images to a right eye viewing port and conducting the other image to a left eye viewing port;
   means, associated with said viewing means, for modifying the perception of one or both images by the patient to differ from the perception required for normal viewing of the images to exercise corresponding one or both eyes of the patient; and
   operator means for controlling the location of said first image element, said operator means operable by the patient to move said first image element while the patient views through said viewing ports.

26. An eye training device for treating amblyopia in a patient, comprising:
   image display means for displaying first and second images, at least one of said first and second images having a first image element whose location is changeable relative to other image elements;
   image viewing means for optically conducting one of said images to a right eye viewing port and conducting the other image to a left eye viewing port;
   means, associated with said viewing means, for occluding image conduction to the viewing port for the non-amblyopic eye of the patient; and
   operator means for controlling the location of said first image element, said operator means operable by the patient to move said first image element while the patient views through said viewing ports.

27. The training device of claim 26 in which said means for occluding includes a removable optically opaque element.

28. The training device of claim 26 in which said means for occluding includes filter means for controllably diminishing the conduction of one of said images to the corresponding viewing port for the non-amblyopic eye.

29. The training device of claim 28 in which said image display means includes means for transmitting said first and second images as polarized light and said filter means includes polarizing means positionable to have an axis of polarization different from that of said polarized light.

30. The training device of claim 29 in which said polarizing means has an adjustable axis of polarization.

31. The training device of claim 26 in which said image display means includes means for altering the location of other image elements in at least one of said first and second images.

32. An eye training device for treating myopia in a patient, comprising:
   image display means for displaying first and second images visually superimposable into a single image, at least one of said first and second images having a first image element whose location is changeable relative to other image elements;
   image viewing means for optically conducting one of said images to a right eye viewing port and conducting the other image to a left eye viewing port;
   refractor lens means proximate each viewing port for establishing normal refractory viewing of said first and second images at a viewing distance of optical infinity;
   concave lens means, located proximate at least one of said viewing ports, for partially compensating for myopic refractive errors of one or both eyes of the patient; and
   operator means for controlling the location of said first image element, said operator means operable by the patient to move said first image element while the patient observes said first and second images through said viewing ports.

33. The training device of claim 32 in which said image display means includes means for altering the location of other image elements in at least one of said first and second images.

34. The training device of claim 33 in which said means for altering includes:
   image signal means for generating location control signals; and
   means, responsive to said location control signals, for varying the location of said other image elements.

35. The training device of claim 32 in which said right and left eye viewing ports are spaced apart with respect to each other to enable binocular use of said device by the patient.

36. The training device of claim 32 in which said refractor lens means and said concave lens means are part of an interchangeable lens assembly.

37. An eye training device for enhancing accommodation in a patient, comprising:
   image display means for displaying first and second images visually superimposable into a single image;
   image viewing means for optically conducting one of said images to a right eye viewing port and conducting the other image to a left eye viewing port;

a bifocal lens assembly for relaxing the accommodative mechanism in one or both eyes of the patient in a first position relative to said left and right eye viewing ports and for stimulating the accommodative mechanism in a second position; and means for moving said bifocal lens assembly to and from said first and second positions.

38. The training device of claim 37 in which said image display means includes means for establishing a first image element in at least one of said first and second images, means for establishing at least one other image element in at least one of said first and second images, and means for altering the location of said first image element relative to said other image element.

39. The training device of claim 38 further including operator means for controlling the location of said first image element, said operator means operable by the patient to move said first image element while the patient observes said first and second images through said viewing ports.

40. The training device of claim 37 in which said bifocal lens assembly includes a convex lens for relaxing the accommodative mechanism.

41. The training device of claim 37 in which said bifocal lens assembly includes a concave lens for stimulating the accommodative mechanism.

42. The training device of claim 37 in which said means for moving includes user activation means actuatable by the patient to move said bifocal lens assembly.

43. The training device of claim 42 in which said activation means includes:
linkage means connected proximate its first end to said bifocal lens assembly; and
user control means, connected proximate a second end of said linkage means, for selectively relocating said second end.

44. The training device of claim 42 further including means for rewarding the patient when said user activation means is actuated at a preselected rate.

45. The training device of claim 37 in which said bifocal lens assembly provides the same relaxation and stimulation for both eyes.

46. The training device of claim 37 in which said image viewing means includes refractor lens means proximate each eye viewing port for establishing normal refractory viewing of said first and second images at a selected viewing distance.

47. The training device of claim 46 in which said refractor lens means establishes said viewing distance as a reading distance.

* * * * *